United States Patent [19]

Meibauer

[11] Patent Number: 5,400,811
[45] Date of Patent: Mar. 28, 1995

[54] POWER DRIVEN TOOTH FLOSSER

[76] Inventor: Robert H. Meibauer, 77 5th St., Highlands, N.J. 07732

[21] Appl. No.: 126,386

[22] Filed: Sep. 24, 1993

[51] Int. Cl.6 .............................................. A61C 15/00
[52] U.S. Cl. .............................................. 132/322
[58] Field of Search .............. 132/309, 321, 322, 323, 132/327, 329, 324

[56] References Cited

U.S. PATENT DOCUMENTS

| | | |
|---|---|---|
| 3,421,524 | 1/1969 | Waters . |
| 3,534,745 | 10/1970 | Waters . |
| 3,552,022 | 1/1971 | Axelsson . |
| 3,667,483 | 6/1972 | McCabe ............................ 132/322 |
| 3,759,274 | 9/1973 | Warner ............................ 132/322 |
| 3,828,804 | 8/1974 | Ely . |
| 3,835,872 | 9/1974 | Daniel . |
| 3,847,167 | 11/1974 | Brien ............................. 132/322 |
| 3,927,686 | 12/1975 | Zambito . |
| 4,014,354 | 3/1977 | Garrett . |
| 4,162,687 | 7/1979 | Lorch . |
| 4,307,740 | 12/1981 | Florindez et al. . |
| 4,338,957 | 7/1982 | Meibauer ......................... 433/122 |
| 4,458,702 | 7/1984 | Grollimund ....................... 132/322 |
| 4,586,521 | 5/1986 | Urso ............................... 132/322 |
| 4,830,032 | 5/1989 | Jousson ........................... 132/323 |
| 5,069,233 | 12/1991 | Ritter ............................. 132/322 |

Primary Examiner—Cary E. O'Connor
Attorney, Agent, or Firm—Harold James; Robert L. Epstein

[57] ABSTRACT

A power driven tooth flosser utilizes lengths of conventional dental floss, provides a length of that floss held in place to facilitate its insertion between teeth of the user, and then causes that length of floss to be driven in axial reciprocation, thereby to provide optimum and safe removal of plaque and debris from between the teeth.

9 Claims, 4 Drawing Sheets

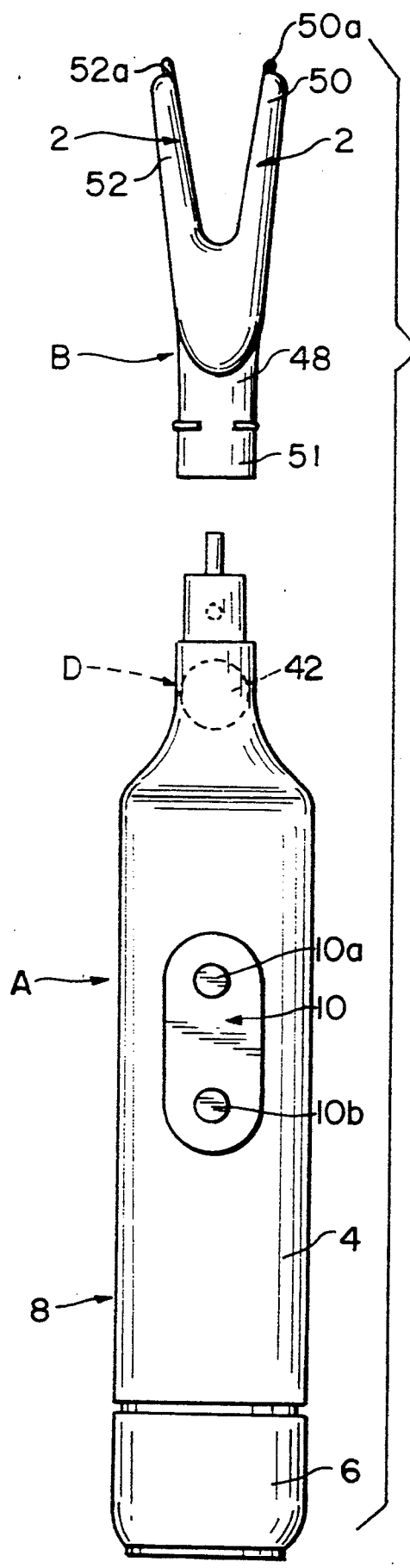
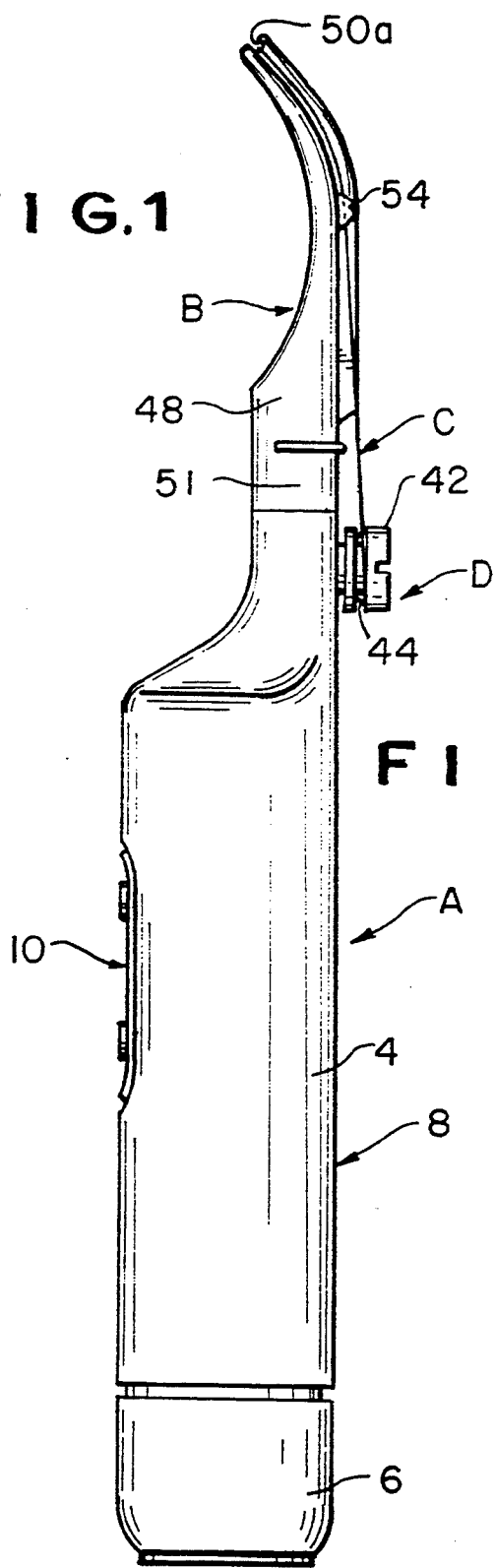

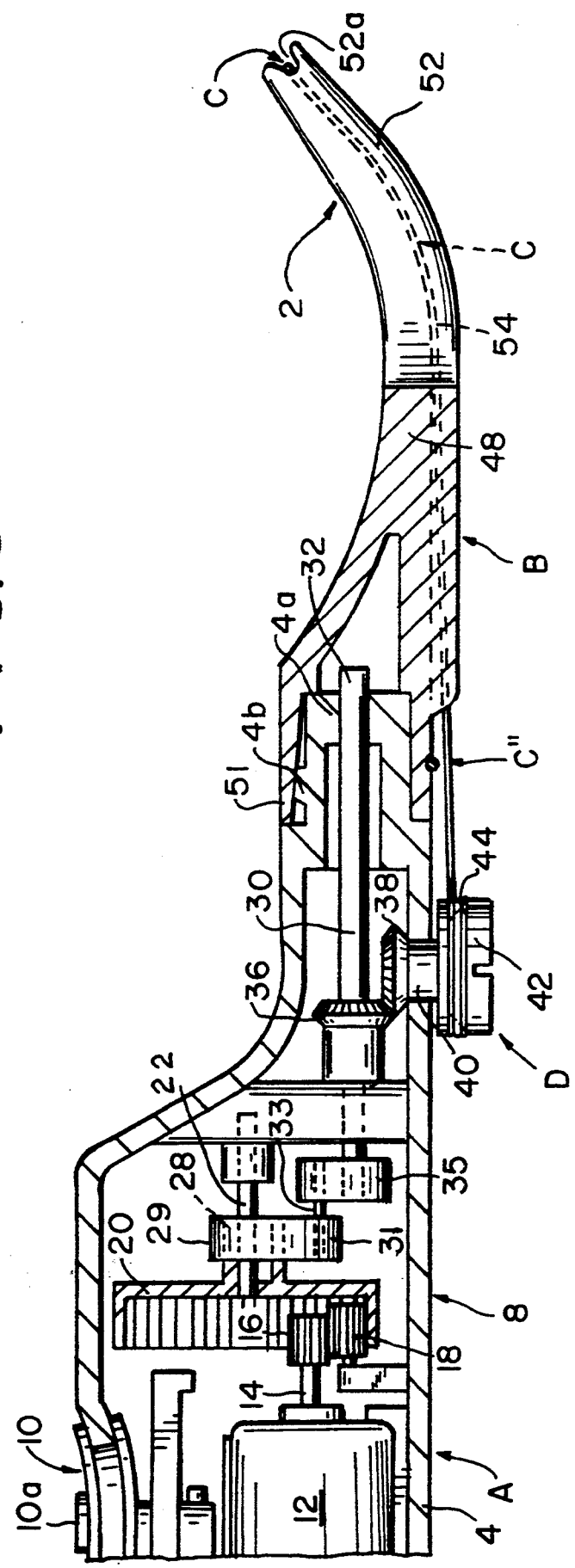

FIG. 6
FIG. 7
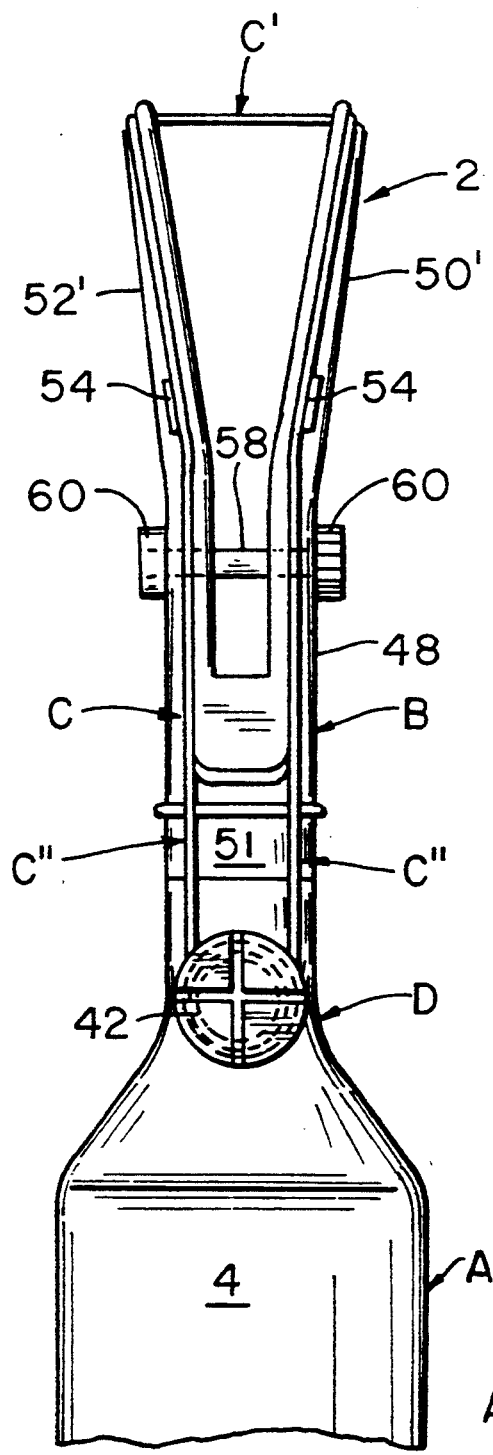
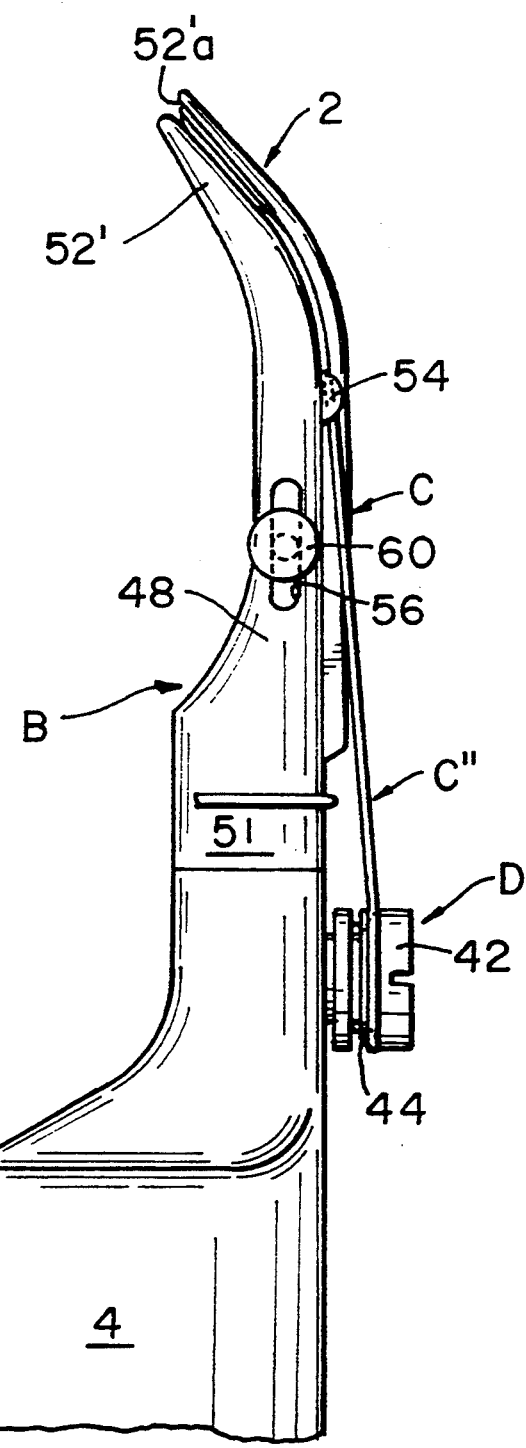

POWER DRIVEN TOOTH FLOSSER

The present invention relates to a power driven tooth flosser, and in particular to one which utilizes ordinary dental floss and causes that floss to axially reciprocate, thereby to enhance its prophylactic action, by means of an exceptionally simple and effective structure.

BACKGROUND OF THE INVENTION

It is well known in the field of dentistry that failure to remove plaque from dentition surfaces and debris from between dentitions is a principal cause of dental diseases, such as tooth decay and gingivitis and the like. Removal of plaque and debris by brushing is the commonest and easiest method known. However, brushing is generally inadequate, especially when self-administered. A more efficient and known technique is the cleaning of the dentition surfaces and areas between such surfaces by using a dental tape or floss (hereinafter generally termed "floss") which is moved reciprocally over and between the dentition surfaces. Furthermore, the reciprocating motion of the floss as it is manipulated over and between the dentition surfaces is beneficial as a treatment for and prevention of periodontal diseases, such as gingivitis and the like. This is so since the free margin of the gingiva which is adjacent to the individual teeth of the dentition and forms the gingival sulcus can be readily reached by dental floss, although it is generally inaccessible to a brush or other instruments, and the sulci are subject to the invasion of plaque or colonies of bacteria which cause diseases of these tissues. Thus, floss, in general, is particularly beneficial in removing plaque and debris, as well as serving, in .addition, as a vehicle for the application of medication. On the other hand, dental tape or floss is inconvenient and awkward to handle.

Consequently, much development has been undertaken in the past to provide dental tape or floss in various forms which is more convenient to handle and use. In addition, much development has taken place to provide mechanical devices for the flossing of dentition surfaces. Therefore, past developments have broadly involved the provision of dental tape or floss in various forms to render the same easier to use and the provision of mechanical devices to support or hold the dental tape or floss in a manner so that it can be employed with greater efficiency and facility.

As an example of such developments, U.S. Pat. No. 4,162,687 discloses a flossing device which is manipulated by hand and provided with a pair of spaced, resilient arms having fingers extending therefrom. The fingers are equipped with knobs on their distal ends and a length of dental tape or floss having a gromet on each end is disposed over the knobs on the ends of the fingers. A somewhat similar device, but which is power driven, is disclosed in U.S. Pat. No. 4,014,354 in which the dental tape or floss is tensioned between a pair of L-shaped arms attached to a handle which is adapted to be driven by the power element. On the other hand, U.S. Pat. No. 3,927,686 discloses a hand manipulated flossing device which includes a handle and an adjustable head provided with a single strand or a plurality of strands of dental tape or floss.

Still another dentition cleaning device is disclosed in U.S. Pat. No. 3,835,872 in which a flexible dental tape or floss is disposed on a handle having a detachable yoke for tautly supporting a run of the tape, the tape being attached to a pair of anchor pins disposed on the handle and one of which is disposed on a reciprocable trigger mounted in the handle for the purpose of tensioning the tape. The tape per se is provided with non-elastic loops at each end which are disposed over the previously mentioned pins. U.S. Pat. No. 3,828,804 discloses still another apparatus which is a hand manipulated device for cleaning teeth that includes a handle with a nub disposed thereon and which is provided with extending, spaced arms having notches at the ends thereof. An endless or circular elastomeric dental floss or tape is disposed in the notches thereby passing across the space between the arms and around the nub. In a variation of the device a simple length of elastomeric band is anchored in the notches of the arms by means of shims or heads.

A further dentition cleaning instrument is disclosed in U.S. Pat. No. 3,759,274 in which a strand of dental floss is mounted on an extended fork which supports the strand and permits an oscillating movement which is imparted thereto by a drive means. In addition, the device also includes a spool for carrying the strand and for registering a new, unused portion of the strand for use in each subsequent cleaning cycle. A still further dentition cleaning device is shown in U.S. Pat. No. 3,667,483 in which the device includes a pair of projecting arms disposed on a support frame, the arms being provided with guides at their outer ends to receive and permit relative movement of floss which passes from a spool to a take-up reel mounted on the supporting frame. The floss is driven in a reciprocating manner through a device provided with means to alternately remove floss from the supply spool and feed it to the take-up spool after each use.

In U.S. Pat. No. 3,552,022 there is disclosed another powered dentition cleaning or polishing device in which a tool having a conical stem portion is adapted to be inserted in and removed from a handle in which a reciprocating socket is provided therefor. The operating end of the tool is wedgelike and pointed, two broad sides being rough in order to abrade dentition surfaces and a third side therof being narrow and smooth in order to prevent injury to the gingiva. Another power driven cleaning device is disclosed in U.S. Pat. No. 3,534,745. The device includes a housing provided with spaced prongs and a dental tape or floss holder and supply unit adapted to be removably attached to a power unit which imparts reciprocating motion to the tape as well as permitting the feeding of new tape to the unit after each .use. Finally, U.S. Pat. No. 3,421,524 discloses a power driven dentition cleaning device including a power unit which is adapted to receive a cleaning unit which includes an elongated shaft provided with a pair of spaced tynes. A dental tape or floss supply holding member is removably positioned on the power unit and the dental tape or floss is fed therefrom through an eyelet in each of the tynes and back to the supply holding member where it is taken up on a take-up spool.

Mention may also be made of U.S. Pat. No. 4,307,740 of Dec. 29, 1981, U.S. Pat. No. 4,830,032 of May 16, 1989, and U.S. Pat. No. 5,069,233 of Dec. 3, 1991, all of which involve devices in which the floss is held in fixed position relative to the structure which supports it, and that structure, along with the floss, is power driven.

While the various devices disclosed in the above-mentioned patents are useful for cleaning dentition surfaces, they still exhibit various disadvantages. For example, many of them are extremely complex in structure and consequently relatively expensive to manufacture. In addition, many of the known structures are relatively difficult to employ, often being difficult to load and requiring complex adjustment to impart the required tautness to the dental tape or floss utilized therewith.

In addition, many of the known devices do not provide maximum contact of the floss with the dentition surfaces to be cleaned and, in addition, due to their construction, necessitate the use of more than the needed amount of dental tape or floss for carrying out a given cleaning operation.

The disadvantages of the above-described devices have been substantially completely eliminated by the device and process of my U.S. Pat. No. 4,338,957 of Jul. 13, 1982. In that patent there is disclosed a dental prophylaxis device which comprises in combination housing means provided with an axial cavity and having a pair of spaced tynes provided with slotted openings disposed thereon and projecting outwardly therefrom, stationary support means on the housing in the vicinity of the base of each of the tynes and oscillating support means located on the housing between the bases of the tynes and which is supported on a cylindrical sleeve that is disposed axially within the cavity of the housing, the housing means being adapted to be connected to driving means to drive the oscillating support means through the cylindrical sleeve.

The dental prophylaxis process comprises contacting dentition surfaces to be treated with a dental floss having a thread segment which is provided with a non-elastic loop at one end and an elastic loop at the opposite end, reciprocating the thread segment over the surfaces of the dentition to be treated, while expanding and contracting the elastic loop in response to the application of tensile force to the dental floss as it reciprocates over the dentition surfaces and absorbing the tensile force which is imparted to the dental floss when it encounters resistance as it reciprocates over the dentition surfaces and the elastic loop expands.

While my previous device and process have substantially completely eliminated the disadvantages of the above-described device, there still exists, however, the need for such a device and process which exhibit even further improvement. The present invention fulfills this need. In particular, it eliminates the need to use any specially prepared or constructed length of floss and enables the user to employ lengths of floss severed when needed from conventional spools of floss such as are readily available in any pharmacy, while at the same time not only holding the floss in position where it may readily be inserted between adjacent teeth but also causing that floss when inserted to reciprocate axially and thus produce optimum prophylactic action. This is all accomplished by an exceedingly simple and highly effective mechanism. Means may also be provided for varying the resistance of the active floss to deformation when in use.

It is therefore the prime object of the present invention to devise an improved and simplified power driven tooth flosser in which the power drive causes the floss to axially reciprocate while it is in position between adjacent teeth.

It is a further object of the present invention to provide a flosser causing the floss to axially reciprocate which can use lengths of ordinary floss such as are generally readily available.

It is another object of the present invention to provide a tooth flosser of the type described in which the degree of resistance of the active floss length to deformation may be adjusted.

BRIEF DESCRIPTION OF THE DRAWINGS

To the accomplishment of the above, and to such other objects as may hereinafter appear, the present invention relates to the construction of a motor driven tooth flossing device as defined in the appended claims and as described in this specification, taken together with the accompanying drawings in which:

FIG. 1 is a front elevation exploded view of a preferred embodiment of the present invention with the floss-carrying part separated from the handle part of the apparatus;

FIG. 2 is a side elevational view of the device of FIG. 1 with the two parts assembled and with dental floss in place;

FIG. 3 is a cross-sectional view on an enlarged scale of a portion of the device of FIG. 2;

FIGS. 6 and 7 are similar to FIGS. 4 and 2 respectively but of an alternate embodiment of the present invention.

DETAILED DESCRIPTION

Figure 4:
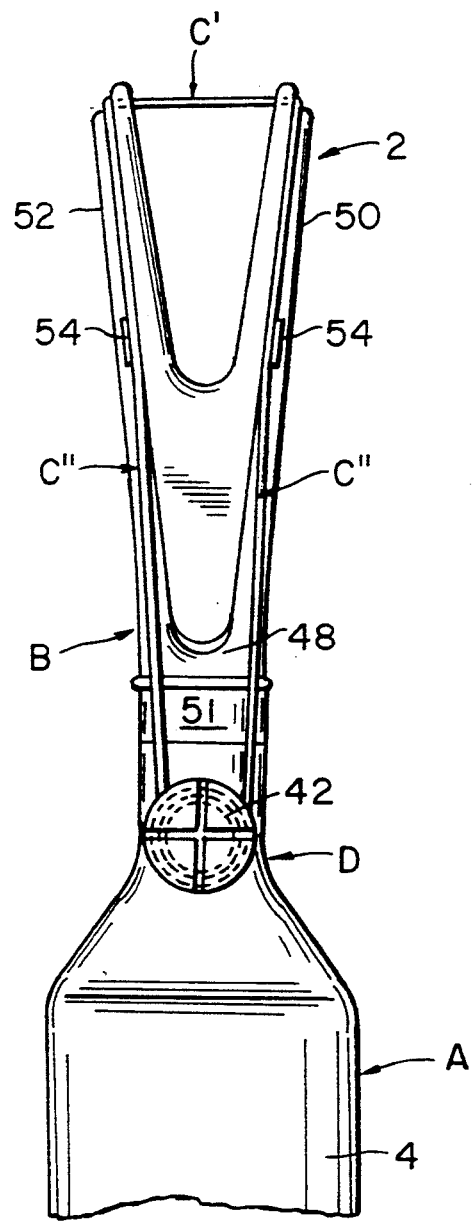
FIG. 4 is a front elevational view of a portion of the device of FIG. 2.

The preferred embodiment of the present invention here specifically disclosed comprises two separate parts generally designated A and B, part A comprising the handle part and containing the power drive and batteries and the part B, removably attached to the part A, carrying a forked structure 2 across the tines 50, 52 of which the dental floss C is adapted to extend. The device also includes an element generally designated D to which the ends of the floss C are adapted to be connected and which, when activated by the power drive, causes the floss to reciprocate axially in the space between the tines 50, 52 of the forked structure 2. The part B may be mounted on and dismounted from the part A simply by sliding it into and out of place. The part B carrying the floss-receiving structure 2 can be substituted for by a part which carries motor driven tooth brushing elements, as is shown and claimed in a copending application of Gary C. Bauman entitled "Power Driven Toothbrush", Serial No. 08/125,784, Sep. 24, 1993.

The handle part A which may be grasped by the user comprises a casing 4 having a removable end cap 6, the lower end 8 of the casing 4 being adapted to receive batteries when the end cap 6 is removed and to make appropriate electrical connection between those batteries, a control switch 10 exposed on the upper portion of the casing 4 and a motor 12 mounted within the casing 4. The motor has an output shaft 14 carrying a pinion gear 16 which meshes with a second pinion 18 rotatably mounted within the casing 4 on a fixed axis and in turn meshing with an enlarged internally toothed gear 20 rotatably mounted in the casing 4 on fixed axis 22. The gear 20 carries, preferably integral therewith, an off-center ring 28 intersected by the axis 22. Rotatably mounted on the exterior of the ring 28 is a looped portion 29 of an arm 31 which extends out radially beyond the gear 20 and which carries a pin 33 which in turn is rotatably mounted in crank arm 35 which is fast on shaft 30, the shaft 30 being journaled in the forwardly extending portion 4a of the casing 4 and extending longitudinally outwardly therefrom at 32. The shaft 30 carries miter gear 36 which meshes with the miter gear 38 on shaft 40 extending out through the casing 4 and carrying an exposed jam cleat 42 with tapered peripheral groove 44.

The switch 10 specifically here shown has two operating buttons 10a and 10b, depression of button 10a being effective to energize the motor 12 and depression of button 10b being effective to de-energize the motor 12. When the motor 12 is energized its output shaft 14 will rotate, thus rotating pinion gears 16 and 18 and internally threaded gear 20, this causing rotation of the ring 28 in an off-center fashion about the axis 22, that movement will be transferred to the arm 35 by the part 29, 31, causing that arm 35 to oscillate back and forth, which in turn causes the jam cleat 42 to oscillate back and forth in rotation.

The section B comprises a body 48 having a lower cylindrical portion 51 slidably receivable over the portion 4a of the handle casing 4 with a friction fit, which fit can be enhanced by providing a projecting portion 4b on the casing portion 4a which frictionally engages the inner surface of the cylindrical portion 50 of the body 48. The body 48 terminates in the forked structure 2 defined by separated tines 50 and 52 the tips of which are provided with grooves 50a and 52a respectively designed to receive a length C' of the dental floss C, the ends C" of that length of floss extending down to the jam cleat 42 so as to be clampingly received within the peripheral groove 44 of that jam cleat, the two ends of the length of dental floss being wound about the jam cleat 42 in opposite directions. The tines 50 and 52 are gently curved forwardly and their tips are so spaced from one another that the portion C' of the dental floss C can be readily introduced into the space between the user's teeth when the device is assembled and manipulated. The end portions C" the floss which extends toward the jam cleat 42 are guided over the exposed surface of the tines 50 and 52, and projections 54 extend up from the surface of he body 48 against which the floss lengths C" may ride, thus guiding and supporting the floss C when it has been put in place.

Hence when the part B is put in place on the part A and a length of dental floss C has been installed as indicated and the motor 12 is energized the shaft 30 will be oscillated back and forth, the jam cleat 42 will be similarly oscillated in rotation, and hence the floss length C will be axially reciprocated. This will provide for optimum flossing action when the floss length C' is inserted between the teeth of the user, since back and forth movement of thus-positioned floss helps to dislodge and remove material from between the teeth.

Figure 5:
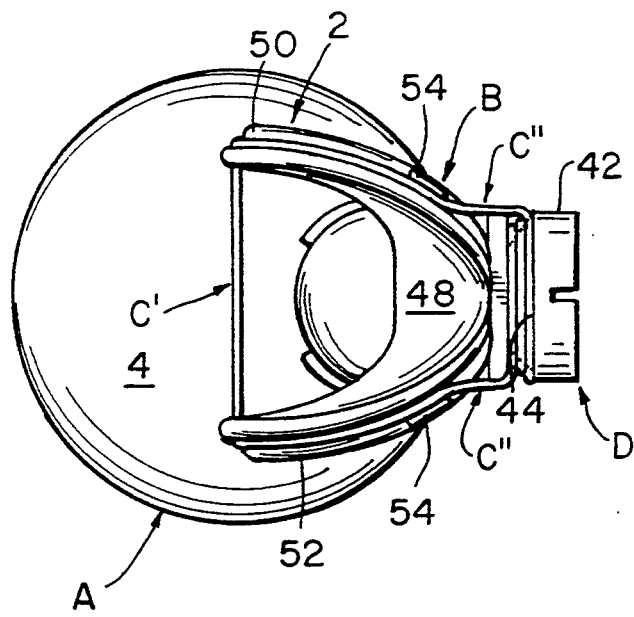
FIG. 5 is a top plan view of the device of FIG. 2.

The material of which the tines 50 and 52 are made is such that those tines have a predetermined amount of flexibility, and this flexibility in turn controls the tension on the floss length C' which is between the teeth. If that tension is too great the interdental structures, both soft and hard, may be traumatized. In the embodiment of FIGS. 1-5 that flexibility is fixed. In the embodiment of FIGS. 6 and 7, however, that flexibility may be altered. In that latter embodiment the tines 50' and 52' are longer than their counterparts in the first described embodiment, and the tines 50' and 52' are provided with elongated slots 56 through which a pin 58 extends, the ends of the pin 58 projecting out laterally beyond the tines 50' and 52' and there threadedly receiving nuts 60 which, when threaded onto the ends of the pin 58, engage the tines 50', 52' and retain the pin 58 in its adjusted position along the length of the slots 56. The closer the pin 58 is positioned to the upper ends of the slots 56 the shorter will be the effective flexing length of the tines 50'. 52' and hence the greater will be their resistance to bending. In this way the flexibility of the tines 50', 52' may be adjusted within limits, and as a result the tension on the active floss length C may be varied, which in turn varies the degree to which that length of floss C' resists deformation from its former straight line condition. By this means the device may be adjusted to the needs or desires of the user.

It is to be understood that the device and process of this invention provide a mechanical flossing means for the removal of plaque on the inter-proximal surfaces of the teeth and, as such, are much more efficient than hand-flossing methods. Moreover, the device and process of this invention eliminate many of the problems inherent in previous devices since the floss can be attached to the mechanical portions of the device in a matter of seconds, and conventionally available floss, such as that normally purchased in long lengths wound on a spool, can be used by severing appropriate lengths of floss from the spool supply and mounting that floss on the flosser, which mounting can be readily accomplished without requiring any particular degree of skill. After the floss has been thus mounted and the active portion thereof is inserted between adjacent teeth the power drive can be actuated and the floss will then reciprocate axially, as is prophylactically desirable. With the device and in accordance with the process, the floss moves rapidly and conforms to the contours of the dentition surfaces without loss of speed or creating slack as often occurs in known devices and the entire dentition surface can be flossed efficiently in a matter of minutes. Furthermore, as previously mentioned, the tines themselves do not move as in some known devices, thus obviating the danger of damaging tissue and dental surfaces by abnormally sharp contact of the tines therewith.

It is also to be noted that the device can be used advantageously by all age groups, from pre-school age children to adults and, moreover, the device can be utilized with great facility by a parent to floss a child's teeth. In addition, the entire device is easily cleaned or sterilized, thus providing hygienic benefits.

The reciprocal action of the floss is beneficial in treating and preventing periodontal disease, that is, gingivitis, since the sulci between the teeth can be reached easily by the dental floss used with the device. Moreover, the mechanical action of the device, in accordance with the process, debrides the tissues of bacterial colonies, necrotic tissue and organic debris, accomplishing this without irritation, while at the same time providing a stimulating effect which promotes the formation of the hornified layer of cells that normally protects the underlying tissues from trauma and bacterial invasion. In addition, if desired the structure can be readily modified so as to provide for adjustment of the tension exerted on the active length of the floss, thus permitting the resistance of that floss length to deformation to be modified within limits. Numerous other advantages of the inventive device and process will be readily apparent to those skilled in the art.

It is to be understood that the descriptive embodiments of this invention set forth herein are illustrative only and the concepts of this invention are not to be limited thereby, except as defined in the appended claims.

I claim:

1. A power-driven tooth flosser comprising a housing, a pair of stationary tines extending therefrom adapted to receive and support a length of dental floss extending therebetween, said length of floss having a pair of free ends extending therefrom beyond said tines, an exposed oscillatable part mounted on said housing, means on said part for receiving said pair of free floss ends, and drive means in said housing operatively connected to said part for driving it in oscillation, whereby, when said part is driven in oscillation, said floss translates back and forth between said tines.

2. The tooth flosser of claim 1, in which said drive means drives said part in rotary oscillation.

3. The tooth flosser of claim 2, in which said oscillatable part comprises a jam cleat for fixedly receiving both of said floss length free ends.

4. The tooth flosser of any of claims 1-3, in which said housing comprises first and second separable housing parts, said first housing part containing said drive means and said second housing part containing said tines.

5. The tooth flosser of any of claims 1-3, in which said housing comprises first and second separable housing parts, said first housing part containing said drive means and said oscillatable part and said second housing part containing said tines.

6. The tooth flosser of any of claims 1-3, in which said housing comprises first and second separable housing parts, said first housing part having an end to which said second housing part is adapted to be secured and containing said drive means, said drive means comprising a shaft exposed at the end of said first housing part, and means for operatively drivingly connecting said oscillatable part to said shaft when said housing parts are assembled.

7. The tooth flosser of claim 6, in which said oscillatable part is mounted on said first housing part.

8. The tooth flosser of any of claims 1-3, in which said housing has an end and sides, said tines extending from said housing end, said oscillatable part being exposed at a side of said housing.

9. The tooth flosser of claim 8, in which said housing comprises first and second separable housing parts, said first housing part containing said drive means and said oscillatable part and said second housing part containing said tines.

* * * * *